United States Patent [19]
Calvo et al.

[11] Patent Number: 5,455,007
[45] Date of Patent: Oct. 3, 1995

[54] UNIVERSAL STRIPPER PLATE

[75] Inventors: Manuel Calvo, Miami; Nicholas Parker; James N. Hoskinson, both of Sunrise; Etzer Ketant, North Miami; Kyriakos Christou, Miami Lakes, all of Fla.

[73] Assignee: Coulter Corporation, Miami, Fla.

[21] Appl. No.: 250,265

[22] Filed: May 27, 1994

[51] Int. Cl.⁶ .................................................. G01N 35/10
[52] U.S. Cl. .............................. 422/100; 422/63; 422/99; 422/104; 141/165; 141/177; 141/312; 73/864.21; 73/864.23; 436/48; 436/49; 436/180
[58] Field of Search ............................. 422/63, 100, 104, 422/103, 64, 65; 436/43, 47, 48, 49, 54, 55, 174, 180; 73/864, 864.01, 864.23, 864.21; 141/165, 177, 312

[56] References Cited

U.S. PATENT DOCUMENTS

| | | | |
|---|---|---|---|
| 3,991,627 | 11/1976 | Laird et al. | 73/423 R |
| 4,387,076 | 6/1983 | Cabrera et al. | 422/67 |
| 4,478,095 | 10/1984 | Bradley et al. | 73/864.27 |
| 4,609,017 | 9/1986 | Coulter et al. | 141/1 |
| 4,713,218 | 12/1987 | Schwartz | 422/99 |
| 4,713,974 | 12/1987 | Stone | 73/864.23 |
| 4,751,052 | 6/1988 | Schwartz et al. | 422/100 |
| 4,861,553 | 8/1989 | Mawhirt et al. | 422/65 |
| 4,928,539 | 5/1990 | Champseix et al. | 73/864.24 |
| 4,951,512 | 8/1990 | Mazza et al. | 73/861.23 |
| 5,221,519 | 6/1993 | Wuerschum | 422/65 |

Primary Examiner—James C. Housel
Assistant Examiner—Long V. Le
Attorney, Agent, or Firm—John T. Winburn; Mitchell E. Alter

[57] ABSTRACT

A universal stripper plate for operating on a plurality of different types of collection containers or tubes. The universal stripper plate includes a universal button for aligning and seating the various tube stoppers or caps for piercing. The universal button is mounted onto a stripper plate, which can be driven into the tube seating/alignment, tube piercing and aspiration and tube release positions. The universal stripper plate also can include a bar code tab to provide a bar code reference and a piercing needle alignment for the various tubes.

8 Claims, 6 Drawing Sheets

UNIVERSAL STRIPPER PLATE

BACKGROUND OF THE INVENTION

This invention relates generally to piercing specimen collection containers in an automated hematology analyzer. More particularly, the invention is directed to a universal stripper plate for a hematology analyzer which can accept a plurality of different sizes and types of collection containers.

Automated blood and blood cell analyzers are well known. These analyzers typically utilize a portion of a whole or pre-prepared blood sample. When the blood sample is taken from a subject, it usually is placed into a collection container such as a vial or test tube. With the potential of exposure to highly infectious diseases by an operator, such as the HIV virus or hepatitis, the tube is closed, typically by a rubber stopper. Many types of blood sample sampling devices have been developed, generally following the procedure of piercing the tube stopper to aspirate a portion of the blood sample. The needle probe or cannula then is removed from the tube and the stopper maintains the remainder of the blood sample sealed in the tube.

In automated hematology analyzers, such as a STKS hematology analyzer sold by the assignee of the present invention, Coulter Corporation of Miami, Fla., a plurality of the sample collection containers or tubes are placed into a tube carrier or cassette. The cassette then is loaded into the hematology analyzer and moved to an aspiration location. Each tube individually is moved to the aspiration location and pierced through its stopper by a transfer needle and a portion of the sample removed for analysis in the hematology analyzer.

Currently, there are four major types of tubes, each of which has a different size and shape. Alignment of each tube in the aspiration location is verified by a tube sensor or detector. One self-adjusting tube detector which preferably can be utilized in a accordance with the present invention is disclosed in U.S. Ser. No. 08/250,264, entitled "Self-Adjusting Tube Detector", filed concurrently herewith and incorporated herein by reference. At the aspiration location, the hematology analyzer includes a stripper plate which functions to align and seat the tube and stopper for piercing by the transfer needle. Currently, this requires four different stripper plates, one for each type of tube. Further, only one type of tube can be operated on by the respective stripper plates, requiring the cassette to be loaded with only the single corresponding type of tube.

When it is desired to utilize another type of tube, the stripper plate has to be changed to the stripper plate corresponding to the other type of tube. This is not an operator operation, but requires a maintenance type procedure to ensure the stripper plate is mounted and is operating correctly.

It therefore would be desirable to provide a universal stripper plate which can accommodate any of the various types of tubes and which allows full flexibility in handling the different tubes in the hematology analyzer.

SUMMARY OF THE INVENTION

The invention provides a universal stripper plate for operating on a plurality of different types of tubes. The universal stripper plate includes a universal button for aligning and seating the various tube stoppers or caps for piercing. The universal button is mounted onto a stripper plate, which plate can be driven into the tube seating and alignment position. The plate and tube then are moved into piercing, aspiration and tube release positions. The universal stripper plate also can include a bar code tab to prevent erroneous bar code readings from the various tubes.

DESCRIPTION OF THE PREFERRED EMBODIMENTS

Figure 1:
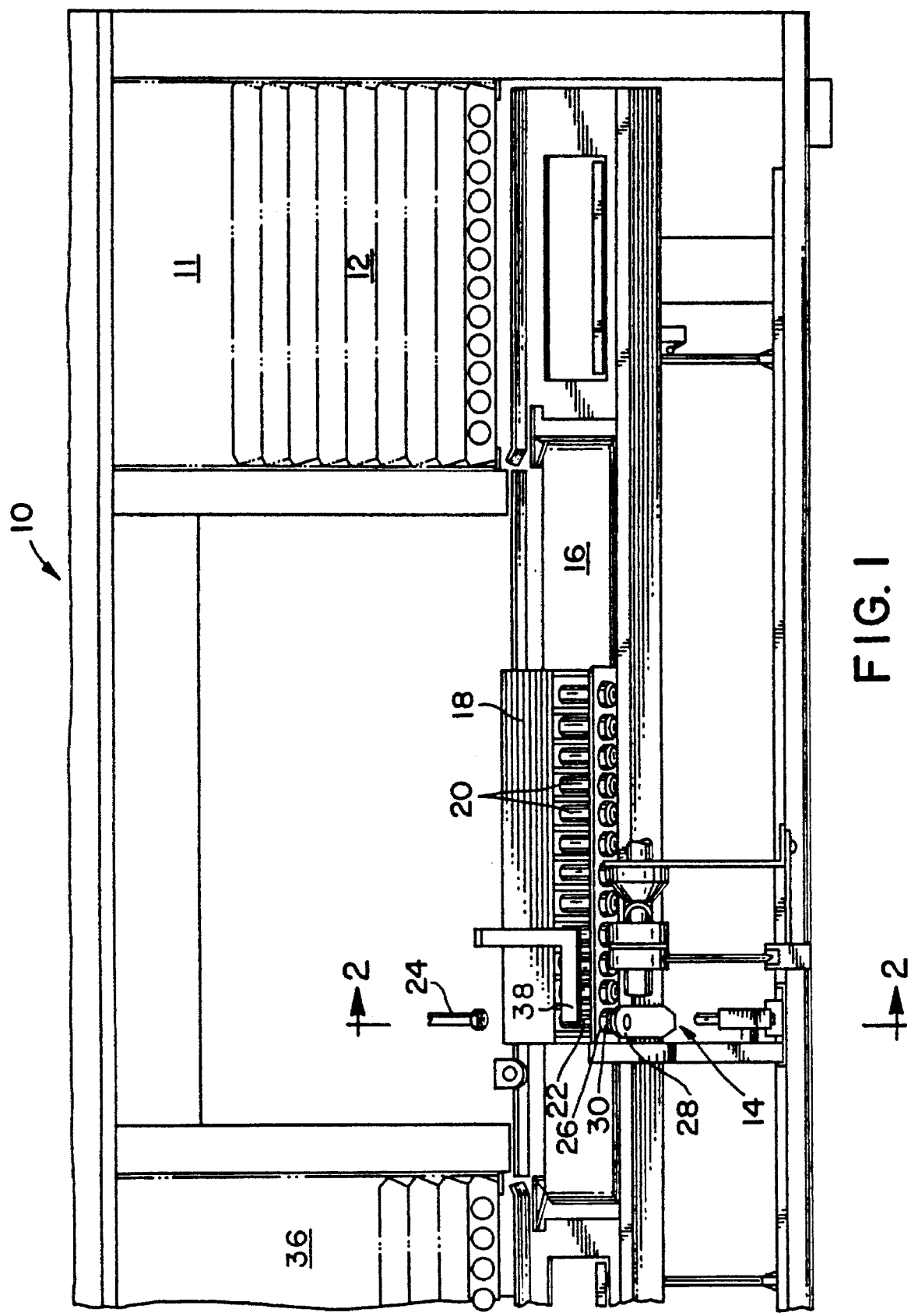
FIG. 1 is a front plan view of one hematology analyzer which can utilize the universal stripper plate of the present invention.
Figure 2:
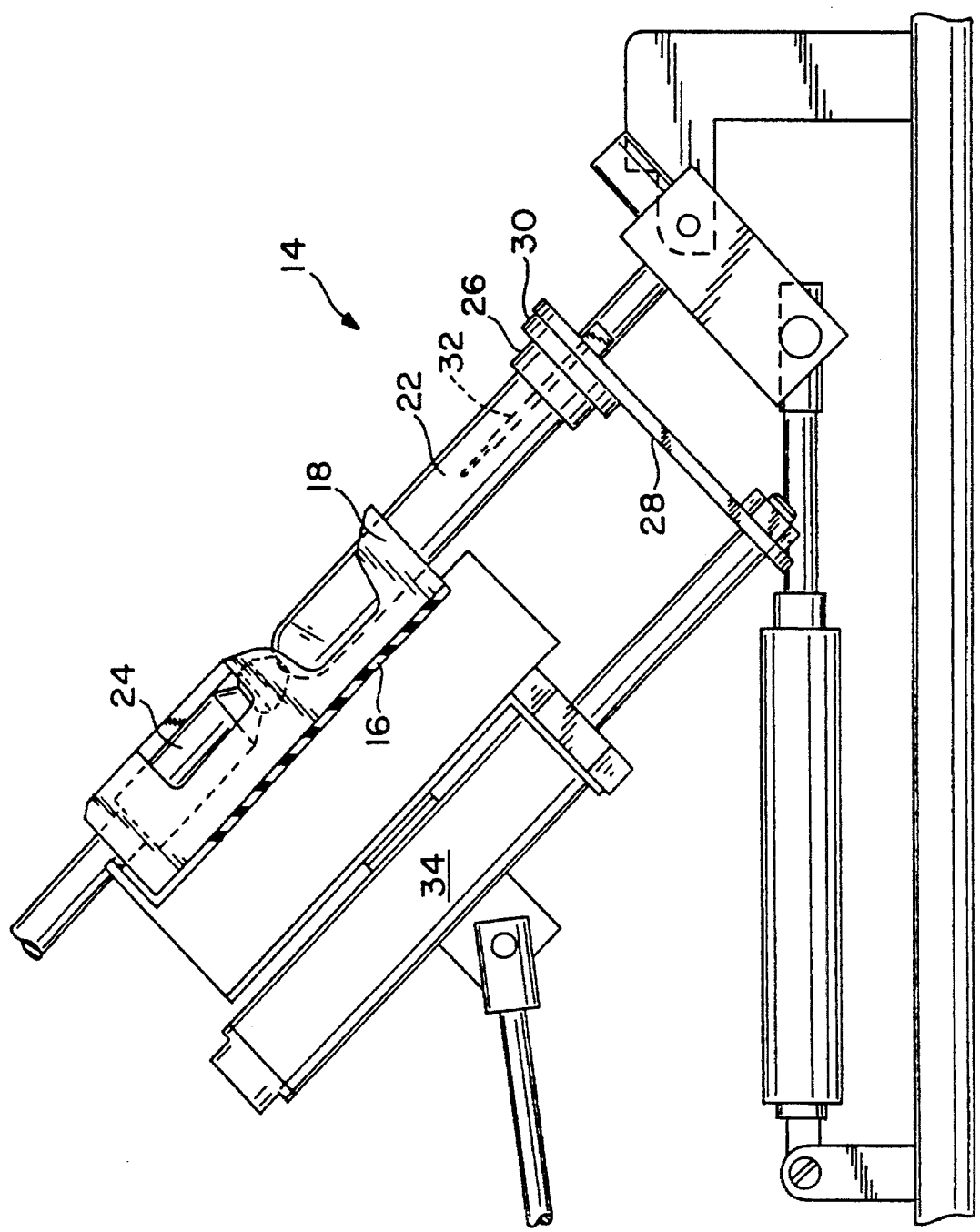
FIG. 2 is a side view of the hematology analyzer taken along the line 2—2 of FIG. 1.

Referring to FIGS. 1 and 2, a hematology analyzer 10 is generally illustrated. Specific details of the operative components are more fully described in U.S. Pat. Nos. 3,549,994 and 4,609,017, which details are not considered essential for a description of the present invention. The hematology analyzer 10 includes a sample collection container or tube input area 11 including a plurality of tube carriers or cassettes 12, which are fed into a piercing and aspiration station 14 by a transport device such as a conveyor belt 16. One tube carrier or cassette 18 is illustrated in the aspiration station 14 containing a plurality of collection containers or tubes 20.

One tube 22 is aligned with a push rod 24, which will push the tube 22 partially out of the cassette 18. The push rod 24 pushes the tube 22 to abut a stopper or cap 26 of the tube 22 against a stripper bar or plate 28. The plate 28 includes a conventional stripper button 30, which aligns the cap 26 with an aspiration probe tip or needle 32, which is driven through the cap 26, typically by the push rod 24. After aspiration, the tube 22 is driven back into the cassette 18, typically by a drive cylinder 34.

Each tube or collection container 20 is in turn moved into the aspiration location and operated on in a similar manner. Once all the tubes 20 in the cassette 18 are aspirated, the tube carrier 18 is moved to an output area 36.

The correct position and alignment of the tube 22 in the aspiration location, aligned with the axis of the aspiration needle 32, must be verified by a sensor 38. As previously referenced, the sensor 38 is located in a fixed position and cannot accommodate various size tubes.

Figure 3:
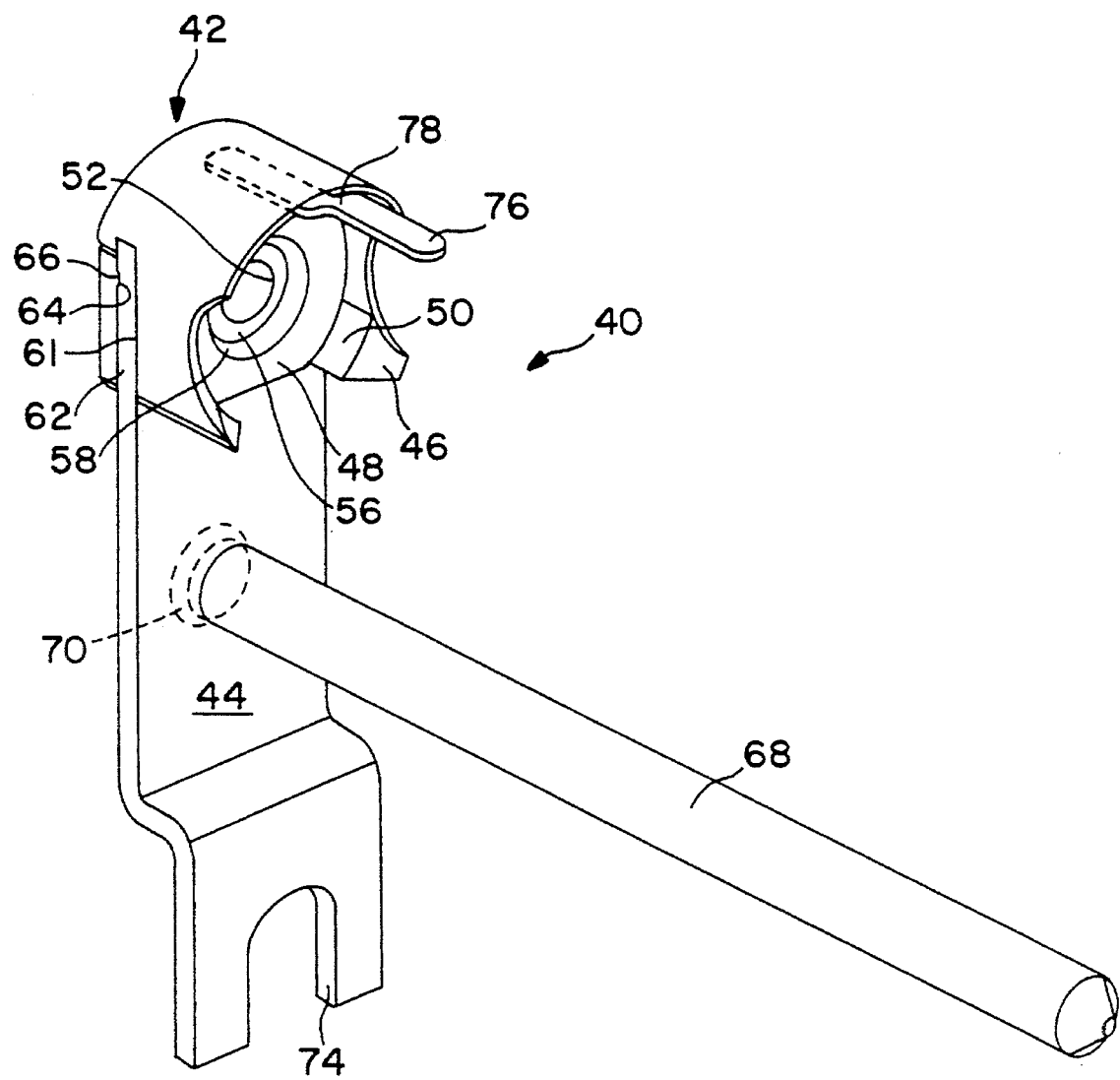
FIG. 3 is a perspective view of the universal stripper plate of the present invention.
Figure 4:
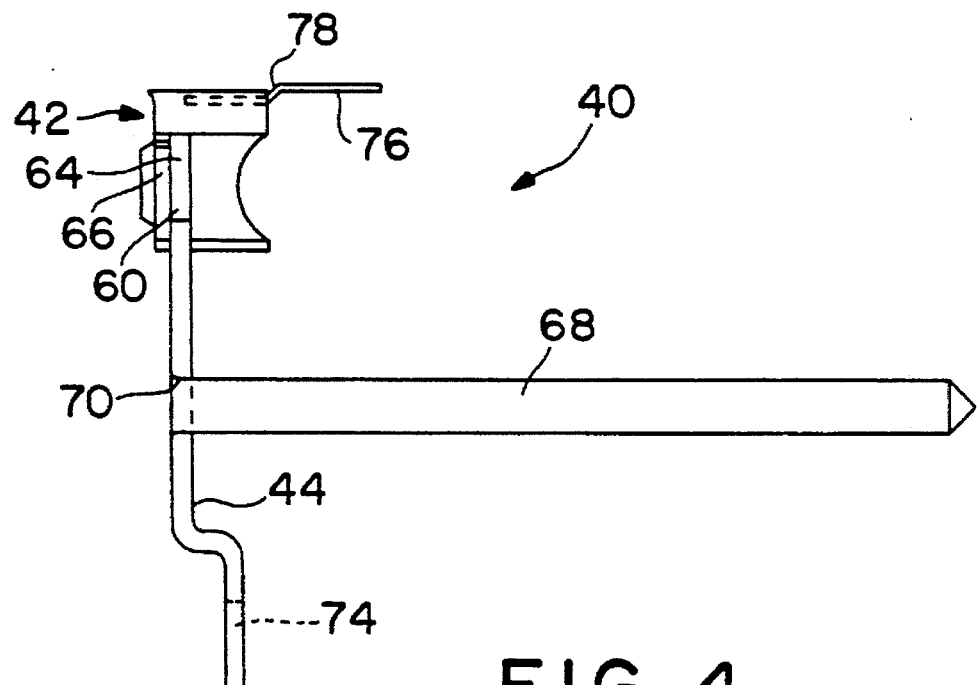
FIG. 4 is a side plan view partially in section of the universal stripper plate of FIG. 3.
Figure 5:
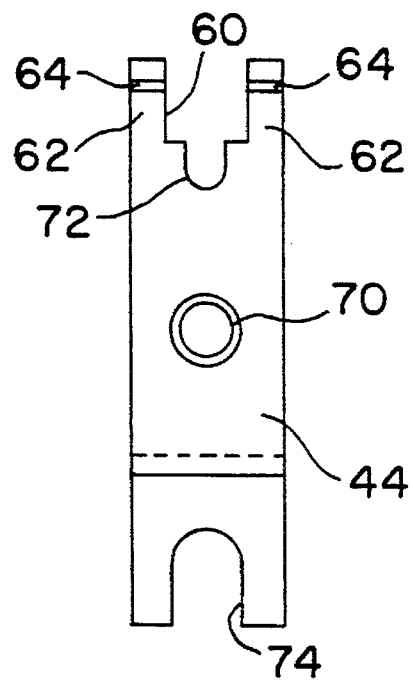
FIG. 5 is a front plan view of the stripper plate of the present invention.

Referring to FIGS. 3–5, an embodiment of a universal stripper plate of the present invention is designated generally by the reference numeral 40. The universal stripper plate 40 is similar in operation to the stripper plate 28 and would replace the plate 28 in the hematology analyzer 10 as well as in similar aspiration operations and analyzers. The universal stripper plate 40 includes a universal button 42, which is mounted on a stripper plate 44.

The universal button 42 preferably is molded in one piece and includes an inclined circumferential inner wall 46 at least around a substantial portion of the universal button 42.

Figure 6A:
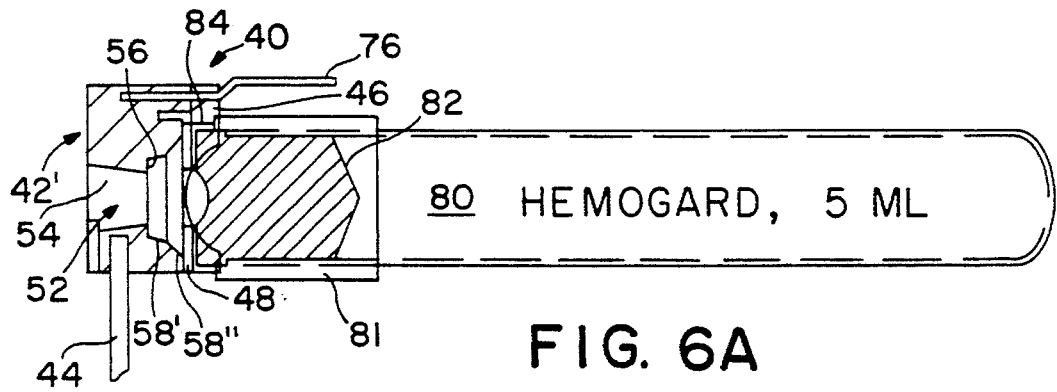
FIGS. 6A-6I are side sectional views of the universal button of the present invention with different types of tubes also in section.

The inclined wall 46 provides an alignment and centering function for a tube 20. A first stopper base 48 is formed adjacent the wall 46 or spaced from the wall 46 by a wall 50. The base 48 accommodates the larger tube stoppers, which are aligned with a central aspiration passageway 52 which is sized to accommodate the passage of the needle 32 therethrough. The passageway 52 also preferably includes an inclined wall 54 (FIG. 6A) to insure that the needle 32 passes through the passageway 52.

The universal button 42 includes at least a second stopper base 56, which also preferably includes an inclined circumferential wall 58 for aligning and centering a smaller tube stopper. The universal button 42 can be mounted onto the stripper plate 44 by adhesive or by screws, but preferably is snap fit such that a worn out or broken universal button 42 easily can be replaced. The universal button can be snap fit into a slot 60 (FIG. 5) in the stripper plate 44. The stripper plate 44 includes a pair of arm portions 62 onto which the universal button 42 is snap fit into complementary outer slots 61 formed in the periphery of the universal button 42. The portions 62 includes grooves 64 into which are inserted a pair of ridges 66 (only one of which is illustrated) formed in the universal button 42.

The universal stripper plate 40 preferably includes a guide rod 68, which is mounted into an aperture 70 formed in the stripper plate 44 by any conventional technique. The universal button 42 can be removed by inserting a bar, tool or screw driver blade (not illustrated) into a release slot 72 (FIG. 5) formed in the base of the slot 60. The stripper plate 44 also preferably includes a slot 74, which accommodates a return drive rod (not illustrated) from the drive cylinder 34.

The universal button 42 also can include a bar code reader or reference flag 76 molded or otherwise mounted onto the universal button 42. The flag 76 signals a bar code reader (not illustrated) to read a bar code (not illustrated) conventionally formed on the tube 22 to be aspirated. The flag 76 also is utilized to verify alignment of the needle piercing axis. The flag 76 preferably includes an offset 78 to allow large tubes 22 to be inserted into the universal stripper plate 44 without interference.

Some examples of the major types of tubes, which can be utilized with the universal stripper plate 40 of the present invention are illustrated in FIGS. 6A–6I. A portion of the universal stripper plate 40, including a sectional view of a button 42' is illustrated with each of the tubes. The button portions are all identified in FIG. 6A with a Hemogard (Trademark of Becton-Dickinson) five (5) ml tube 80. The button 42' includes the inclined wall 46 connected to the base 48, which eliminates the wall 50. The base 56 is connected to the base 48 by two inclined wall portions 58' and 58". The button 42' is otherwise the same as the button 42 previously described.

The tube 80 includes a shoulder 81 and a cap or stopper 82. The shoulder 81 includes a smaller diameter end portion 84 having a face 86. The face 86 of the portion 84 bears against the stopper base 48 and is centered by the wall 46 to ensure alignment of the stopper 82 with the needle passageway 52.

Figure 6B:

FIG. 6B illustrates a Terumo tube 90 sold under the trademark Venoject. The tube 90 includes a large stopper portion 92, which again is aligned by the wall 46 such that a face portion 94 will bear against the base 48. The stopper portion 92 has a very small center aspiration portion 96. The portion 96 again will be aligned by the wall 46 and can bear against the base 48. The recessed base 56 provides relief for the portion 96. If the tube 90 was placed into a stripper plate having only a single base 48, then the portion 96 might not be aligned and the disproportionate forces upon the portion 96 bearing against the base during the needle piercing operation could break the collection container cap 92.

Figure 6C:
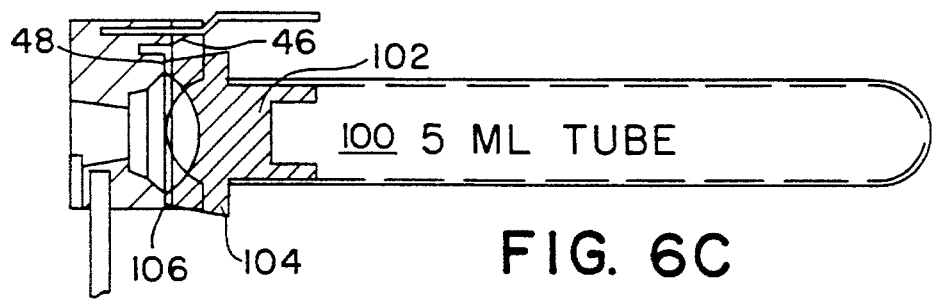

FIG. 6C illustrates a regular five (5) ml tube 100. The tube 100 includes a stopper 102 which has an inclined circumferential wall 104, which aligns the tube 100 with the wall 46 to center a face portion 106 against the base 48.

Figure 6D:
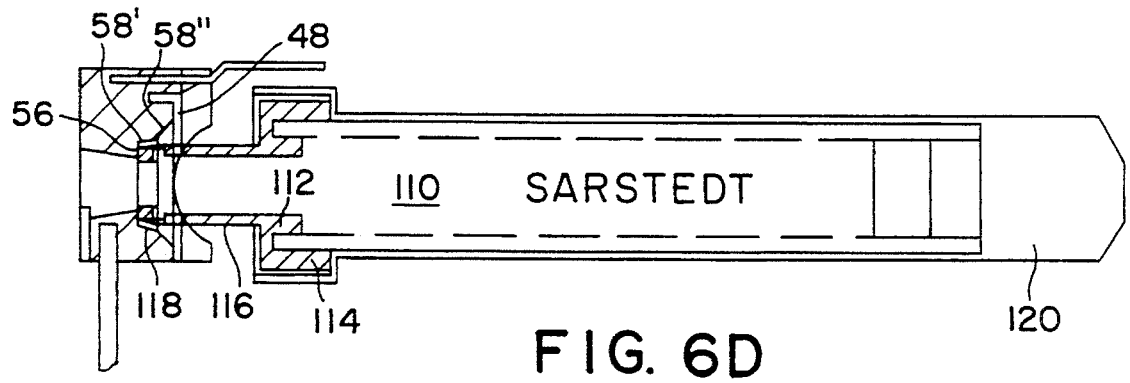

FIG. 6D illustrates a further distinct type of Sarstedt tube 110 sold under the trademark Monovette. The tube 110 includes a very different type of stopper 112, which has a large portion 114 adjacent the tube 110 and a long much smaller aspiration extension 116. The extension 116 includes a beveled end portion 118, which is guided by the Walls 58' and 58" against the base 56. The extension 116 would frequently not be centered and firmly held against the base 56 for error free aspiration in prior art stripper plates.

To accommodate a wide range of tube diameters and types in the analyzer 10, the tube 110 is illustrated inserted into a tube adapter 120, such as disclosed in Ser. No. 08/250,201, entitled "Tube Adapter" filed concurrently herewith and incorporated by reference. The combination of the present invention, the tube adapter 120 and the self-adjusting tube detector also incorporated by reference further extends the size of tube diameters and types which can be utilized in the analyzer 10.

Figure 6E:
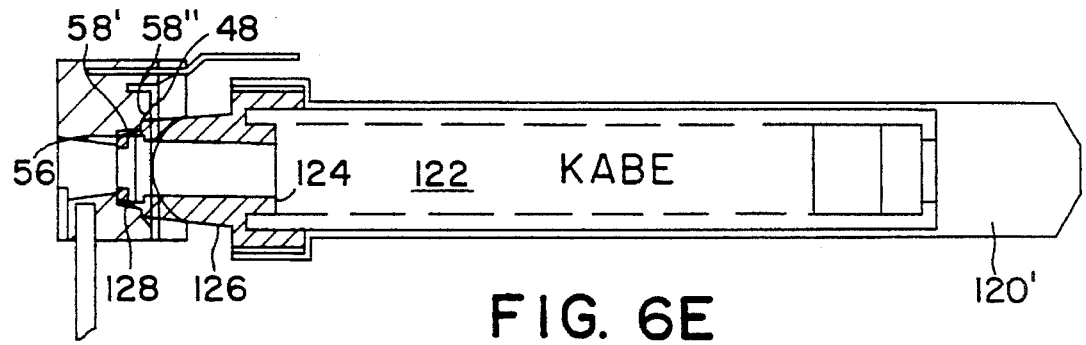

FIG. 6E illustrates yet another type of tube 122 sold by Kabe. The tube 122 also includes a stopper 124, similar to the Sarstedt stopper 112, which has a large portion 126 engaging the tube 122 and a smaller elongated aspiration portion 128 which is tapered and bears against both the wall 58" and the base 56. The tube 122 is inserted into an adapter 120'.

Figure 6F:
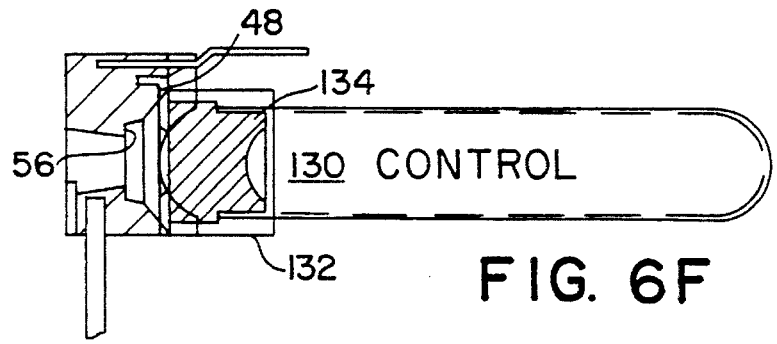

FIG. 6F illustrates a control tube 130 which includes an enlarged shoulder portion 132 which bears against the base 48. The tube 130 includes a recessed stopper 134.

Figure 6G:
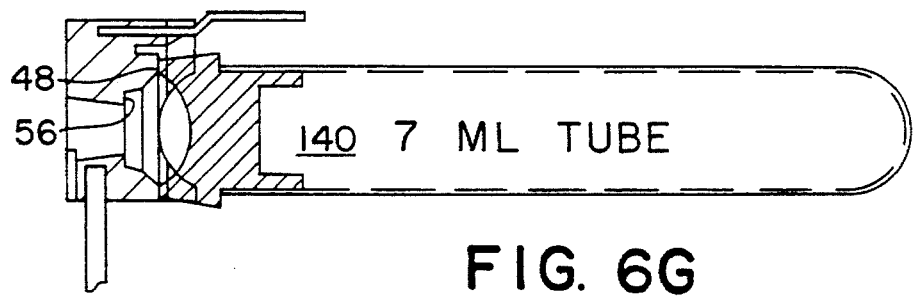

FIG. 6G illustrates a standard seven (7) ml tube 140, which differs from the five (5) ml tube 100 only in size.

Figure 6H:
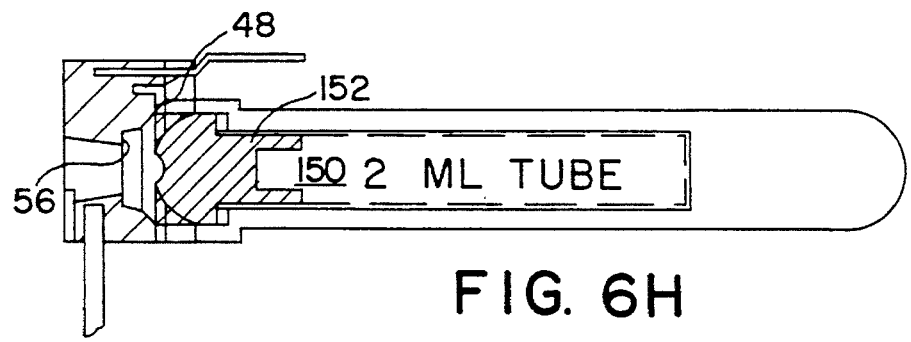
Figure 6I:
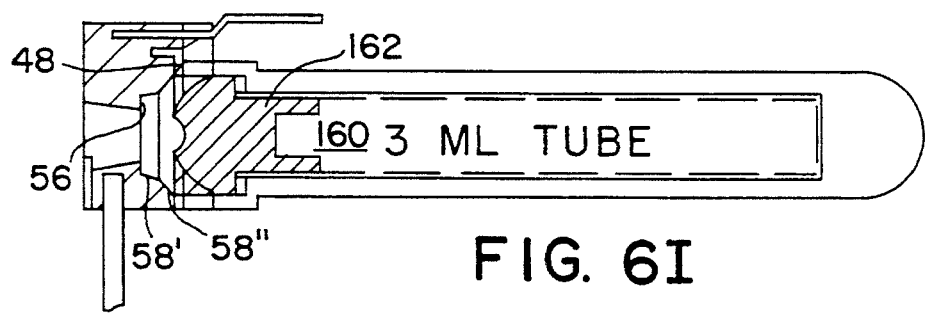

FIGS. 6H and 6I illustrate a two (2) ml tube 150 and a three (3) ml tube 160, which differ only in size and in the size of the tube adapters 120" and 120'" into which they are inserted. The tubes 150 and 160 include respective stoppers 152 and 162 which extend beyond the tubes 150 and 160 against the wall 58", while the adapters 120" and 120'" bear against the base 48.

Many modifications and variations of the present invention are possible in light of the above teachings. It is therefore to be understood that within the scope of the appended claims, the invention may be practiced otherwise than as specifically described.

We claim:

1. A universal stripper plate for a hematology analyzer, the analyzer including means for driving the stripper plate and a sample tube including a tube stopper together for piercing, aspirating, and then releasing the sample tube, said universal stripper plate comprising:

an elongated stripper plate;

a universal button mounted onto a first end of said stripper plate, said universal button including an aspiration passageway formed therethrough and forming an opening in said button at each end of said passageway and including at least two different sized robe stopper bases formed about a substantial peripheral portion of a first one of said aspiration passageway openings, each of said bases accommodating a different sized tube stopper thereon, said first stopper base having a first circumference and a circumferential inclined wall formed at the periphery thereof to provide a first tube guide and alignment structure, and said second stopper base formed with a second circumference smaller than said first circumference and including a second circumferential inclined wall formed substantially between said first stopper base and said second stopper base to provide a second smaller tube guide and alignment structure, said first and second tube guide alignment structures substantially surrounding said first passageway opening; and the analyzer including means for driving the stripper plate and a sample tube including a tube stopper together for piercing, aspirating, and then releasing the sample tube by seating said tube stopper in one of said tube stopper bases.

2. The universal stripper plate as defined in claim 1 including said stripper plate having a slot formed in said first end and said universal button removably mounted into said slot.

3. The universal stripper plate as defined in claim 2 including snap fit means formed on said stripper plate and said universal button for removably snap fitting said universal button onto said stripper plate.

4. The universal stripper plate as defined in claim 3 including said universal button being molded in one piece and said snap fit means including one of a groove and a ridge molded in said universal button and a complementary ridge or groove formed in said stripper plate.

5. The universal stripper plate as defined in claim 1 including a bar code reference and alignment flag formed on said universal button and extending therefrom.

6. The universal stripper plate as defined in claim 1 including said second circumferential wall formed in two inclined portions between said first and said second stopper base.

7. The universal stripper plate as defined in claim 2 including snap fit means formed on said stripper plate and said universal button for removably snap fitting said universal button onto said stripper plate, said universal button being molded in one piece and said snap fit means including one of a groove and a ridge molded in said universal button and a complementary ridge or groove formed in said stripper plate.

8. The universal stripper plate as defined in claim 7 including a bar code flag formed on said universal button and extending therefrom.

* * * * *